(12) United States Patent
Kupce

(10) Patent No.: US 7,598,738 B2
(45) Date of Patent: Oct. 6, 2009

(54) COMPLETE STRUCTURE ELUCIDATION OF MOLECULES UTILIZING SINGLE NMR EXPERIMENT

(75) Inventor: Eriks Kupce, Oxford (GB)

(73) Assignee: Varian, Inc., Palo Alto, CA (US)

( * ) Notice: Subject to any disclaimer, the term of this patent is extended or adjusted under 35 U.S.C. 154(b) by 0 days.

(21) Appl. No.: 12/044,262

(22) Filed: Mar. 7, 2008

(65) Prior Publication Data
US 2009/0224760 A1   Sep. 10, 2009

(51) Int. Cl.
*G01V 3/00*   (2006.01)
(52) U.S. Cl. .................................................. 324/307
(58) Field of Classification Search ............... None
See application file for complete search history.

(56) References Cited

U.S. PATENT DOCUMENTS

| | | | | |
|---|---|---|---|---|
| 5,117,186 | A | * | 5/1992 | Burum et al. ............... 324/307 |
| 5,926,023 | A | * | 7/1999 | De Groot et al. ............ 324/309 |
| 6,064,207 | A | | 5/2000 | Kupce |
| 6,184,683 | B1 | * | 2/2001 | Emsley et al. ............... 324/309 |
| 6,620,589 | B1 | * | 9/2003 | Sem et al. .................... 435/7.1 |
| 6,831,459 | B2 | * | 12/2004 | Szyperski et al. ........... 324/309 |
| 6,838,878 | B2 | * | 1/2005 | Saalwachter et al. ........ 324/307 |
| 6,888,348 | B2 | | 5/2005 | Kupce |
| 7,141,432 | B2 | * | 11/2006 | Szyperski .................... 436/173 |
| 7,396,685 | B2 | * | 7/2008 | Szyperski et al. ........... 436/173 |
| 7,466,127 | B2 | * | 12/2008 | Chandrakumar et al. .... 324/307 |

OTHER PUBLICATIONS

A. Bax, R. Freeman and S. P. Kempsell, J. Am. Chem. Soc., 102, 4849 (1980).
J. Santoro and G.C. King, J. Magn. Reson., 97, 202 (1992).
E. Kupce and R. Freeman, J. Magn. Reson., 99, 644 (1992).
E. Kupce, R. Freeman and B.K. John. J. Am. Chem. Soc., 128, 9606 (2006).
E. Kupce and R. Freeman, J. Magn. Reson., 187, 258 (2007).
F.J.M. van de Ven, Multidimensional NMR in Liquids: basic principles and experimental methods, VCH Publishers Ltd., Cambridge, 1995, pp. 211-224.
F.J.M. van de Ven, Multidimensional NMR in Liquids: basic principles and experimental methods, VCH Publishers Ltd., Cambridge, 1995, pp. 254-265.

* cited by examiner

*Primary Examiner*—Brij B. Shrivastav
*Assistant Examiner*—Dixomara Vargas
(74) *Attorney, Agent, or Firm*—Bella Fishman; David P. Gloekler

(57) ABSTRACT

The complete structure of a molecule of interest is determined from a single NMR experiment utilizing a single NMR pulse sequence. The experiment utilizes the same pulse sequence for acquiring various one-dimensional and multi-dimensional spectra, with independent receivers tuned to individual resonance frequencies.

20 Claims, 5 Drawing Sheets

COMPLETE STRUCTURE ELUCIDATION OF MOLECULES UTILIZING SINGLE NMR EXPERIMENT

FIELD OF THE INVENTION

The present invention relates generally to the use of nuclear magnetic resonance (NMR) techniques to acquire spectral information from sample molecules. More particularly, the present invention relates to NMR experiments that allow determination of the secondary structure of molecules from a single experiment, thereby eliminating the need for recording a series of separate experiments and associated pulse sequences.

BACKGROUND OF THE INVENTION

Various one-dimensional and multi-dimensional (nD) nuclear magnetic resonance (NMR) spectroscopy techniques are presently utilized for elucidating the structure of chemical species. One-dimensional (1D) NMR experiments can provide basic information regarding a sample molecule under investigation such as chemical shifts, sizes of J coupling constants, and relative numbers of nuclear spins. Two-dimensional (2D) NMR experiments provide further elucidation such as connectivity or coupling patterns among spins, and generally resolve information that is left ambiguous or undetected by 1D experiments. NMR experiments of higher dimension (e.g., 3D, 4D, etc.) can provide even further structural elucidation and facilitate the study of spin systems involving three or more nuclei of different types.

A given NMR experiment entails the selection and use of a radio-frequency (RF) pulse sequence that is applied to the sample under investigation via a transmitter coil to generate an observable RF free induction decay (FID) response signal of time domain. The FID signal is detected by a receiver coil and processed by associated receiver electronics. The FID signal is digitized and further processed through one or more dimensional Fourier Transformation (FT) to produce a spectrum of frequency domain from which structural information regarding the sample can be determined. A wide range of pulse sequences or recipes are available for different purposes. Complete elucidation of molecular structure, particularly secondary structure, has conventionally required the successive recording of a number of different NMR experiments to produce a number of different spectra needed for rendering a full analysis of the molecule. This has been due in part to the limited utility of presently known pulse sequences and the limitations of conventional NMR receiver hardware and software. The execution of multiple NMR experiments is disadvantageous for a number of reasons. The carrying out of successive NMR experiments can take a long time, increases the probability of human error and variation in the operating conditions of the NMR spectroscopy apparatus from one experiment to the next, and does not ensure that all spectra are recorded under identical conditions.

A need therefore exists for a single, comprehensive or "all-in-one" NMR experiment capable of recording all of the information necessary for analyzing the structure of a sample molecule with the use of one pulse sequence.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a method is provided for determining the structure of a sample molecule. An NMR pulse sequence is applied to H and X1 nuclei of the sample molecule, wherein H designates a proton and X1 designates a magnetically active heteronucleus. While applying the NMR pulse sequence, two-dimensional X1-X1 correlation spectra are acquired by operating a first RF receiver tuned to the X1 frequency. While applying the same NMR pulse sequence, three-dimensional X1-H correlation spectra are acquired by operating a second RF receiver tuned to the H frequency, the second RF receiver being separate and operated independently from the first RF receiver.

According to another implementation, the NMR pulse sequence is applied to X2 nuclei of the sample molecule in addition to H nuclei and X1 nuclei, wherein X2 designates a magnetically active heteronucleus of a type other than the X1 nucleus. During the same NMR pulse sequence utilized to acquire X1-X1 correlation spectra and X1-H correlation spectra, X2 spectra are acquired.

According to another implementation, the acquisition of X2 spectra includes acquiring X2 spectra based on direct observation of X2 transverse magnetization by operating a third RF receiver tuned to the X2 frequency, the third RF receiver being separate and operated independently from the first RF receiver and the second RF receiver.

According to another implementation, the acquisition of X2 spectra includes acquiring X2-H correlation spectra by operating the second RF receiver.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

The present disclosure provides an NMR technique by which the complete structure of a molecule of interest is determined from a single NMR experiment utilizing a single NMR pulse sequence. By "complete structure" is meant that the secondary structure of the molecule is part of the determination made possible by the single NMR experiment. Generally, this novel technique for implementing comprehensive or "all-in-one" NMR experiments according to the present disclosure may utilize any suitable NMR spectroscopy apparatus. To implement the presently disclosed technique, the apparatus includes a multi-resonance or broadband NMR sample probe equipped with separate, independently operated RF receivers for each nuclear species under investigation. The independent RF receivers may be provided, for example, on respective circuit boards in a console of the NMR spectroscopy apparatus. A portion of the circuitry constituting independent RF receiver channels, such as for example respective pre-amplifiers, may reside with the sample probe as appreciated by persons skilled in the art. The RF receivers are operated in parallel to record several one-dimensional (1D), two-dimensional (2D) and three-dimensional (3D) spectra (or, more generally, n-dimensional or nD spectra) in the single NMR experiment, as necessary to fully elucidate the structure of the molecule under study. NMR experiments as taught herein have been found particularly suitable for analyzing small organic molecules in solution but may be extended to large molecules and solid-state NMR spectroscopy. The NMR experiments are applicable to multiple-spin (or n-resonance) systems. As used herein, H or H-1 designates a proton, X1 designates a magnetically active (NMR-active) nucleus of a given type (e.g., C-13, N-15, P-31, F-19, etc.), X2 designates a magnetically active nucleus of a type different than X1, and so on.

An example will now be described in which one-bond C-C, one-bond C-H, multiple-bond C-H, and multiplicity-edited C-H correlations are recorded in a single NMR experiment. This single experiment is performed utilizing an NMR system equipped with two RF receivers tuned to the proton (H-1) and C-13 frequencies, respectively, to simultaneously record 2-D C-C correlated and 3-D C-H correlated spectra. By this configuration, implementation of the single NMR experiment provides all the spectral information necessary to determine the secondary structure of molecules at the natural abundance of isotopes.

Figure 1:
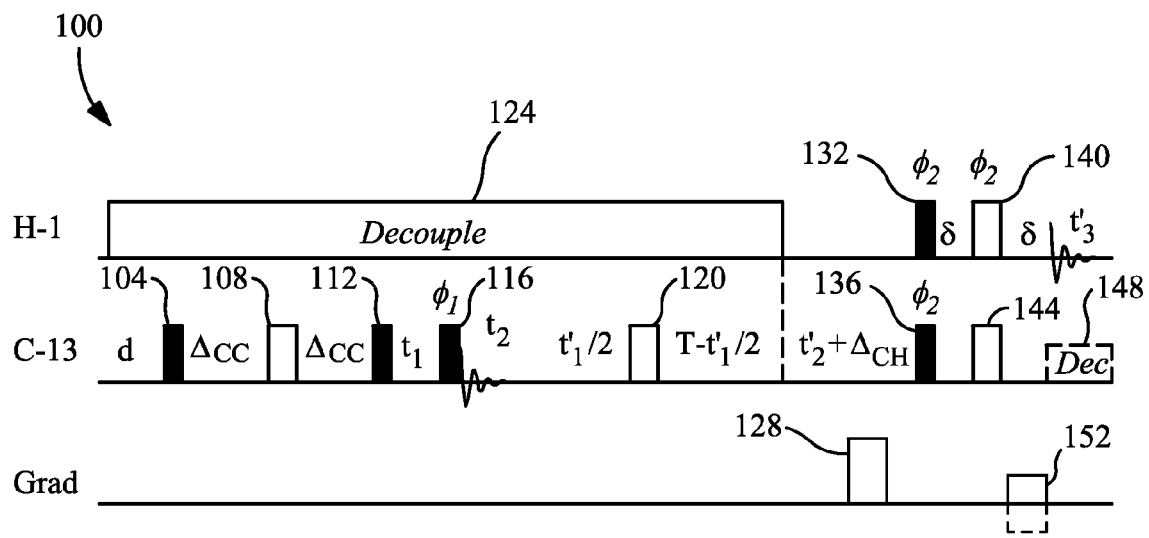
FIG. 1 is an example of a pulse sequence that may be utilized for structure determination of molecules in accordance with the teachings of the present disclosure.

FIG. 1 illustrates an example of a pulse sequence 100 that may be utilized for structure determination of molecules in accordance with the teachings of the present disclosure. According to convention, the first and second horizontal lines illustrate the timing of various pulses applied to H-1 spins and C-13 spins, respectively, and of FID signal acquisitions. Filled-in vertical bars represent 90° pulses and open vertical bars represent 180° pulses. The third horizontal line (designated "Grad") illustrates the timing of field gradient pulses applied by an appropriate field gradient coil to the static ($B_o$) field. In this example, the evolution times $t_1$ and $t_2$ produce the 2D C-C correlation spectrum, while the times $t'_1$, $t'_2$ and $t'_3$ produce the 3D C-H correlation spectrum with 2D sub-spectra for multiplicity editing. The $t'_2$ delay is initially set to $0.5/^1J_{CH}$. The spectral width in the $F'_2$ dimension is set to about $4(^1J_{CH})$. The $\Delta_{CH}$ delay is optional and may be utilized to enhance long-range correlations.

The first part or element of the pulse sequence 100 is a double-quantum C-C correlation sequence such as INADEQUATE (Incredible Natural Abundance DoublE QUAntum Transfer Experiment). This portion of the pulse sequence 100 records a 2-D one-bond C-C correlation spectrum utilizing the first RF receiver, which is tuned to the C-13 resonance frequency. This part of the pulse sequence 100 may generally follow the original recipe as described, for example, in A. Bax, R. Freeman and S. P. Kempsell, *J. Am. Chem. Soc.*, 102, 4849 (1980). Thus, referring to FIG. 1, after an initial delay period d following equilibrium magnetization, a first 90° excitation pulse 104 is applied to generate transverse magnetization in C-13 spins. The first 90° pulse is followed by a spin echo period utilizing a 180° pulse 108 with delays $\Delta_{CC}=0.25/^1J_{CC}$. A second 90° pulse 112 converts anti-phase magnetization generated during the spin echo period to multiple-quantum coherence, which then evolves for a time $t_1$. A third 90° read pulse 116 converts the multiple-quantum coherence back into observable magnetization, which is then recorded for a time $t_2$. The phase cycling of the first receiver is designed to suppress C-13 peaks that are not coupled to other C-13 nuclei. In the conventional INADEQUATE experiment this magnetization is suppressed by phase cycling. However, in the presently disclosed experiment both the single-quantum and double-quantum C-13 coherences are recorded and saved in separate memory locations. The more abundant C-13 single-quantum coherences are then refocused and further utilized to record the C-H correlations.

Thus, following the INADEQUATE acquisition period $t_2$, the C-13 evolution is reversed by a C-13 refocusing pulse 120 and is encoded during a first indirect acquisition period $t'_1$ in a constant time evolution sequence, where the constant time period $T=t_2-t'_2$. See, e.g., J. Santoro and G. C. King, *J. Magn. Reson.*, 97, 202 (1992). As indicated in FIG. 1, the protons are irradiated with any suitable broadband decoupling sequence 124 during the INADEQUATE and constant time evolution sequence portions. The H-1 decoupling 124 is then switched off to allow $J_{CH}$ coupling evolution during a second indirect acquisition period $t'_2$ that is utilized to record 2D multiplicity-edited C-H correlation spectra. The C-13 coherence is then encoded using a gradient pulse 128. As indicated by 90° pulses 132 and 136 of phase 42 applied to the H-1 and C-13 spins, this gradient pulse 128 is followed by C-13 polarization transfer to H-1 for detection. The polarization transfer is followed by a spin echo period, as indicated by 180° pulses 140 and 144 of phase $\phi_2$ applied to the H-1 and C-13 spins, placed between first and second refocusing delay periods of length $\delta$. A gradient decoding pulse is applied during the second refocusing delay $\delta$ to minimize the unwanted H-1 coherences. This delay is set sufficiently long to allow for the gradient pulses and a reasonable gradient recovery time, usually 1 to 1.5 ms in total. An optional binomial filter may be incorporated by incrementing the delay $\delta$ in steps of $0.5/^1J_{CH}$ in successive scans as described previously. See, e.g., E. Kupce and R. Freeman, *J. Magn. Reson.*, 99, 644 (1992). C-13 decoupling 148 is switched on during the acquisition period $t'_3$ at the end of the pulse sequence 100 only for the first three $t'_2$ increments to produce fully decoupled one-bond C-H correlations with multiplicity editing. These increments are omitted in the 3D Fourier transform. The signal is recorded for a time $t'_3$ using the second RF receiver tuned to the H-1 frequency.

The phase cycles utilized are as follows: $\phi_1$=x, y, -x, -y; $\phi_2$=y, -x, -y, x; receivers x, -y, -x, y. The phase sensitive spectra are obtained by incrementing the phase $\phi_1$ and inverting the second gradient 152 for alternate increments (as indicated by the dashed line).

It can be seen that by utilizing the pulse sequence 100 described above and illustrated in FIG. 1, with parallel receivers respectively tuned to the H-1 and C-13 resonances, the various 2D and 3D spectra needed to fully elucidate the structure of a molecule of interest are recorded in a single NMR experiment. Accordingly, multiple pulse sequences and/or experiments are not required.

An example of implementing the process of structure elucidation according to this technique will now be described in the context of a single NMR experiment carried out on a sample of quinine. FIGS. 2-5 illustrate the various spectra recorded for this example. To generate the spectra, a Varian 600 MHz NMR system was operated to implement the pulse sequence 100 of FIG. 1. This system was equipped with two parallel receivers as described above and a room-temperature, triple-resonance (H/C/N) sample probe. Each spectrum in FIGS. 2-5 is scaled at 128 increments in F1 and 16 increments in F2, 4 scans per increment, with spectral widths $sw_1=20$ kHz, $sw_2=12.5$ kHz. The spectra may be interpreted by known techniques.

Figure 2:
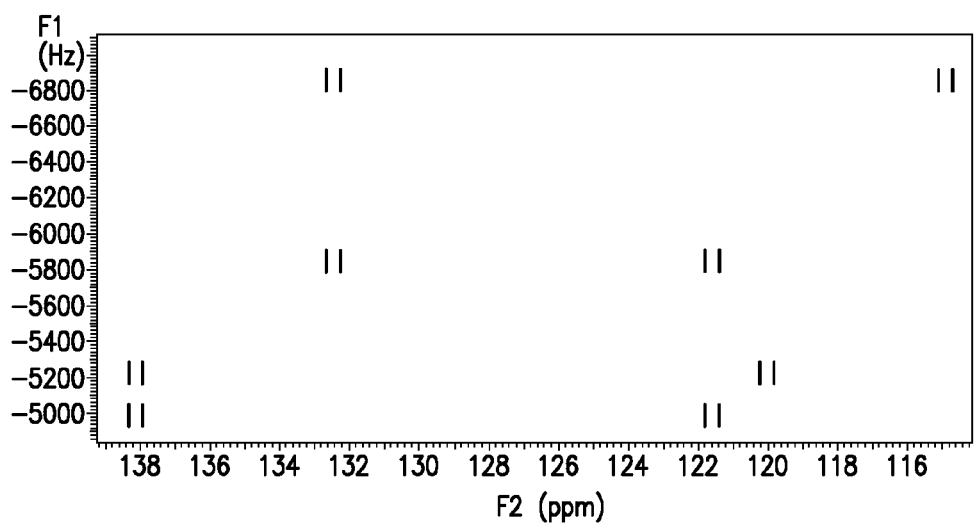
FIG. 2 is a 2D double-quantum (INADEQUATE) spectrum of a sample of quinine acquired by applying the pulse sequence of FIG. 1 in a single NMR experiment.

FIG. 2 is the 2D INADEQUATE spectrum. This spectrum provides the one-bond C-C connectivities, thus allowing one to piece together all C-C chains of the molecule.

Figure 3A:
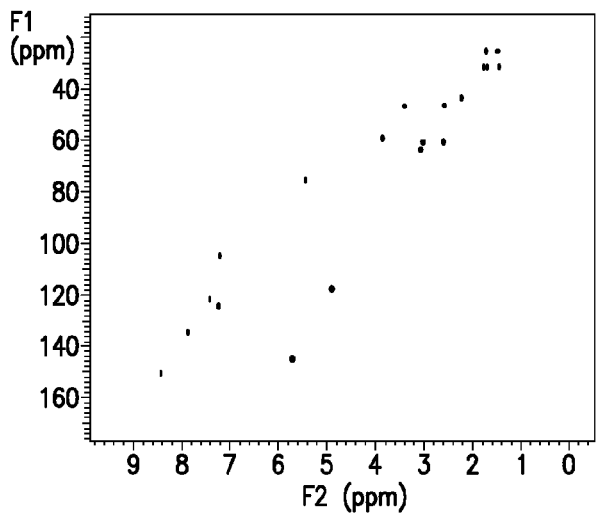
FIGS. 3a, 3b, 3c are 2D C-H HSQC spectra of the quinine sample acquired by applying the pulse sequence of FIG. 1 in the same NMR experiment.
Figure 3B:
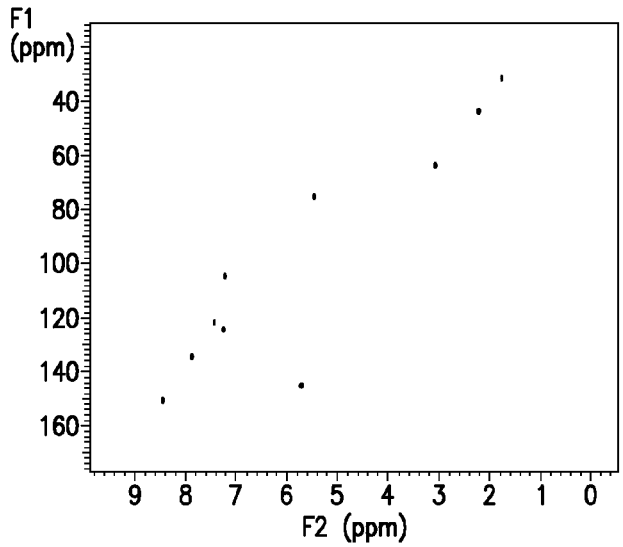
Figure 3C:
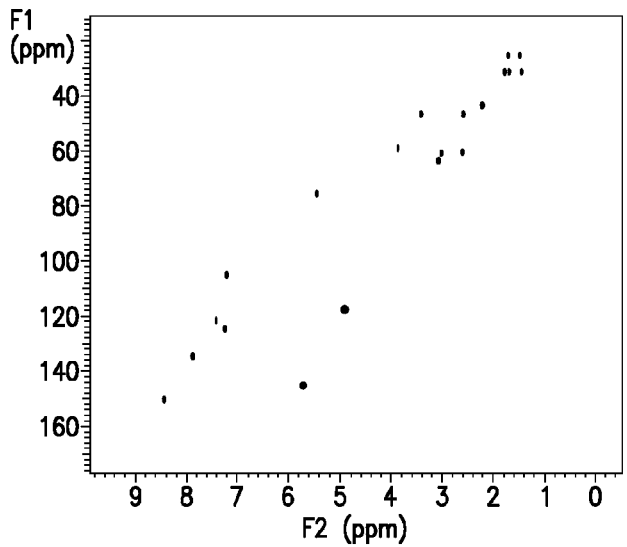

FIGS. 3a-3c are the 2D C-H HSQC (Heteronuclear Single-Quantum Correlation) spectra elucidating one-bond C-H single-quantum correlation obtained from the pulse sequence of FIG. 1. These spectra thus provide one-bond C-H connectivities, showing the protonated carbon atoms in the molecule, and the multiplicity edited C-H HSQC spectra indicate the number of attached protons at each carbon site.

Figure 4:
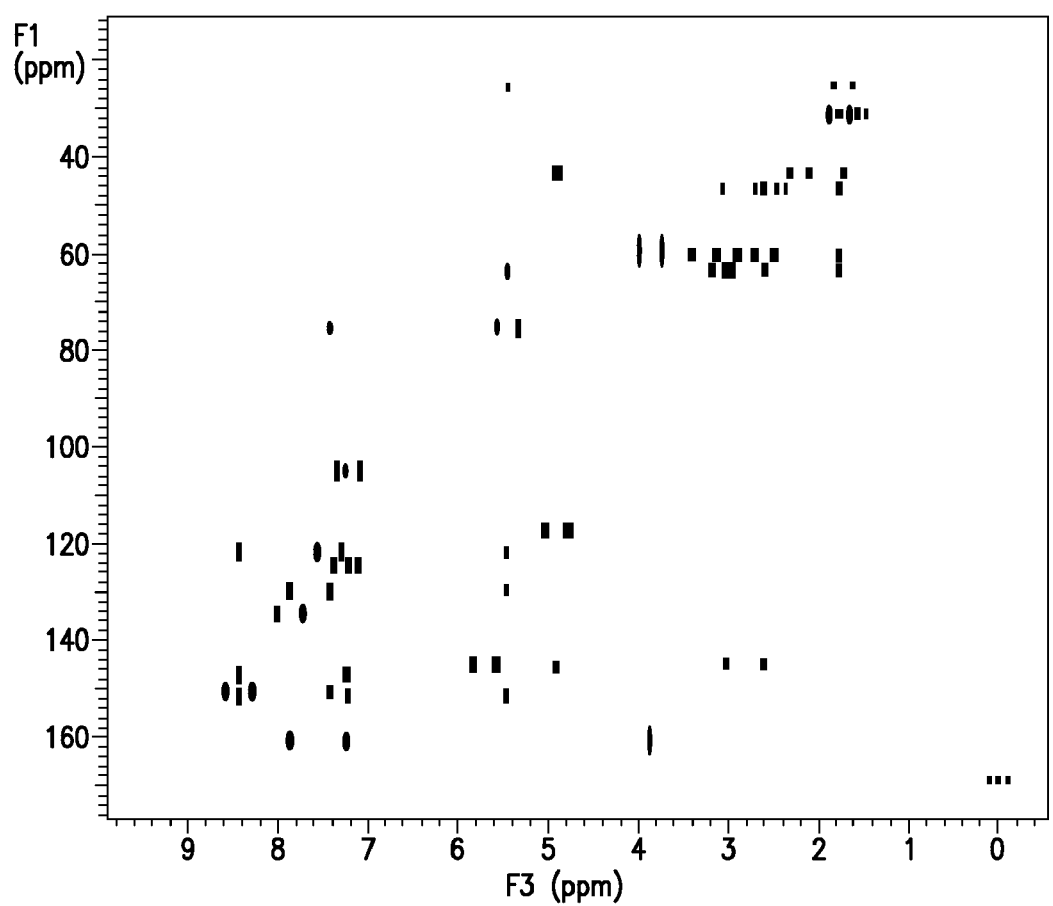
FIG. 4 is a 3D C-H J-HMBC spectrum of the quinine sample acquired by applying the pulse sequence of FIG. 1 in the same NMR experiment.

FIG. 4 is the 3D C-H J-HMBC (Heteronuclear Multiple-Bond Correlation) spectrum. This spectrum provides long-range C-H (multiple-bond) correlations, thus connecting all the fragments into a single molecule.

Figure 5:
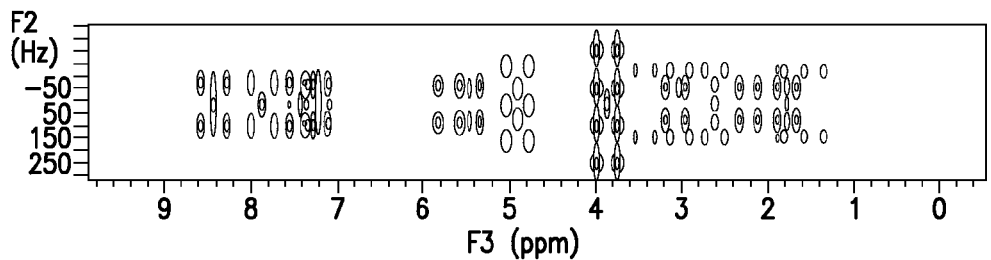
FIG. 5 illustrate F1F3 planes stacked along the F2 dimension of the 3D C-H J-HMBC spectrum of FIG. 4.

FIG. 5 illustrate F1F3 planes stacked along the F2 dimension of the 3D C-H J-HMBC spectrum. It can be seen that the individual planes of the 3D J-HMBC experiment provide additional information about the multiplicity of the long range C-H correlations.

In addition to interpreting the foregoing spectral information, it will be appreciated that any hetero-atoms can be inserted based on the chemical shift information and the number of attached proton and carbon atoms.

It can be seen from the foregoing that the secondary structure of the molecule under investigation (e.g., quinine in the present example) is now fully established. No additional experiments and associated additional pulse sequences are necessary.

Figure 6:
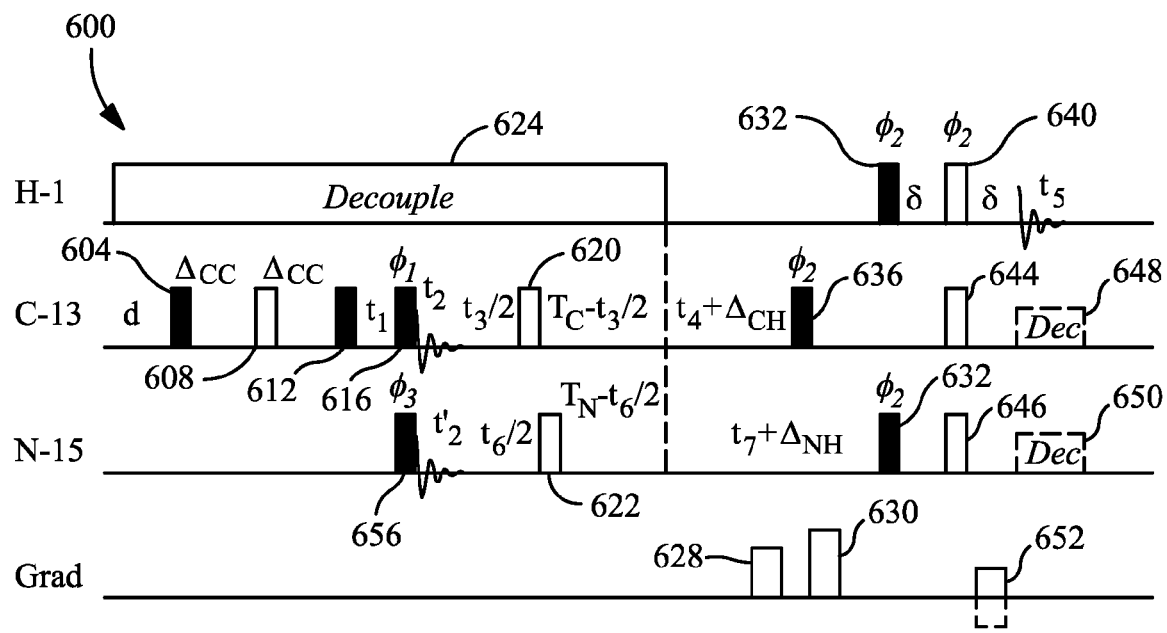
FIG. 6 is another example of a pulse sequence that may be utilized for structure determination of molecules in accordance with the teachings of the present disclosure.

The all-in-one experiment taught in the present disclosure may be extended to include direct observation of other magnetically active heteronuclei, or X-nuclei (e.g., N-15, P-31, F-19, etc.), and time-shared X-H correlations. FIG. 6 illustrates an example of a pulse sequence 600 suitable for recording the additional spectra involved in implementing such an experiment. Various details of this pulse sequence 600 may generally be the same as the pulse sequence 100 described above and illustrated in FIG. 1 and thus their descriptions will not be repeated. The NMR spectroscopy apparatus in this case may include a third independent RF receiver tuned to the X frequency.

The pulse sequence 600 of FIG. 6 will be considered for an example where X=N-15. Given that in typical organic molecules the $^{15}N$-$^{15}N$ couplings are very small or do not exist, no effort is made to record $^{15}N$-$^{15}N$ correlations. Hence, except for a 90° N-15 read pulse 656, the INADEQUATE part of the pulse sequence 600 is omitted for N-15 nuclei. The sequences for broadband proton decoupling 624 and C-13 INADEQUATE (inclusive of pulses 604, 608, 612 and 616) are carried out as described above. Following the C-13 INADEQUATE sequence and the 90° N-15 excitation pulse 656, respective FID signals are recorded for times $t_2$ and $t'_2$ on the C-13 and N-15 channels in the same manner as described above in conjunction with FIG. 1. The phase $\phi_3$ of the 90° N-15 read pulse 656 is the same as the receiver phase. The residual magnetization of both C-13 and N-15 nuclei is then refocused, as indicated by the respective 180° C-13 and N-15 pulses 620 and 622. The subsequent constant-time evolution periods, $t_3$ and $t_6$, are set to satisfy the different chemical shift ranges for C-13 and N-15 nuclei. Due to different the magneto-gyric ratios of C-13 and N-15, the gradient encoding pulses 628 and 630 need to have different strengths. This may be achieved by inserting a C-13 90° coherence transfer pulse 636 between the two gradient pulses 628 and 630 so that C-13 spins are affected by the first gradient 628 only, while the N-15 spins experience the sum of the two gradients 628 and 630. The gradient ratio may be chosen such that the relative area of the gradient pulses 628 and 630 seen by C-13 and N-15 pulses is 4 and 10, respectively, in comparison to the area of the coherence decoding gradient pulse 652. Alternatively, the N-15 and C-13 coherences may be separated at the decoding stage rather than encoding stage following the same recipe.

The C-13 magnetization is then transferred to protons while the N-H couplings are allowed to evolve for additional period of $\Delta_{NH}$ to allow for generally lower values of $^nJ_{NH}$ as compared to $^nJ_{CH}$. The N-15 magnetization is then transferred to protons, and following the H-1 read pulse 632, the coherence decoding gradient sequence is applied. To compensate for smaller N-H couplings as compared to C-H couplings, the C-13 pulse 636 is displaced with respect to the centered H-1 and N-15 pulses 632 and 634 by $0.25(1/^1J_{NH}-1/^1J_{CH})$ seconds. The delay δ is set to $0.25/^1J_{NH}$ seconds.

For applications requiring wide C-13 and/or N-15 bandwidth, the 180° C-13 and N-15 pulses 644 and 646 may be replaced by either composite or adiabatic pulses as described previously. See, e.g., E. Kupce and R. Freeman, *J. Magn. Reson.*, 187, 258 (2007).

Figure 7:
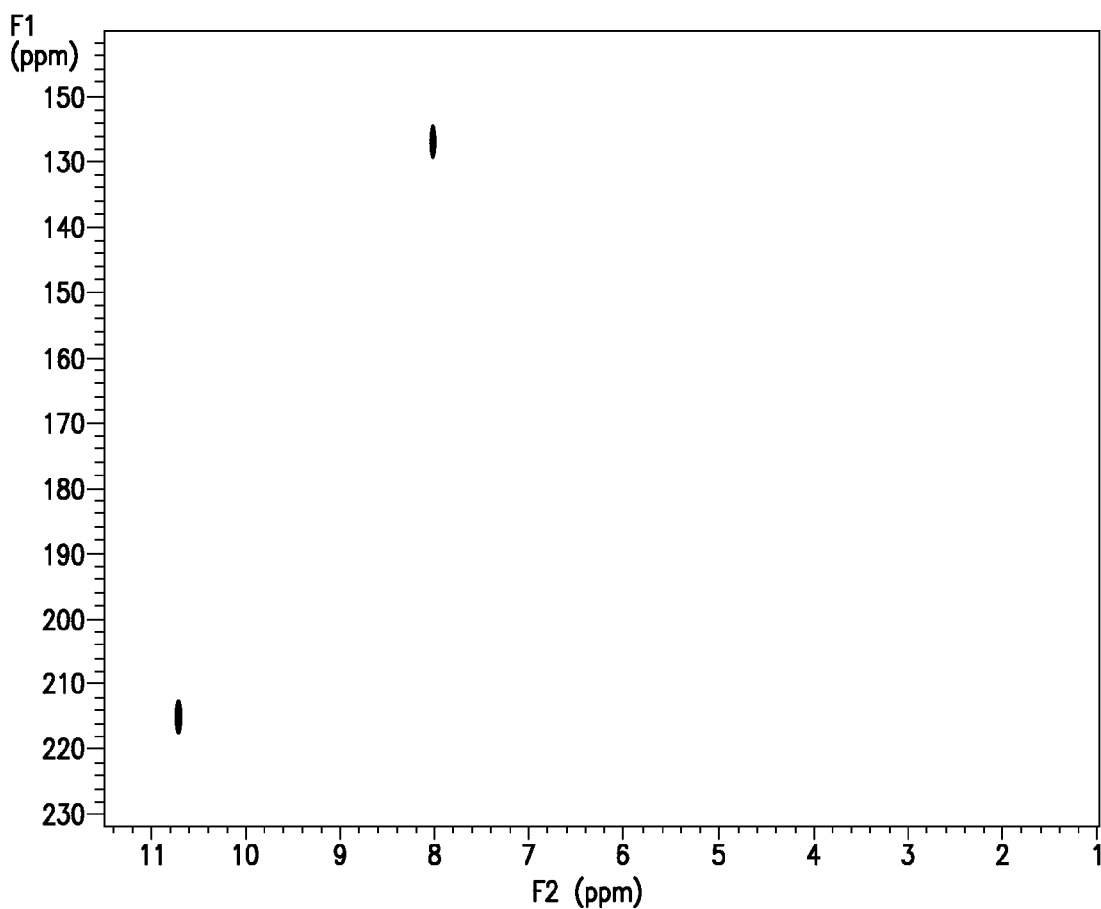
FIG. 7 is 2D N-H HSQC spectra of a sample of melatonin acquired by applying the pulse sequence of FIG. 6 in a single NMR experiment.
Figure 8:
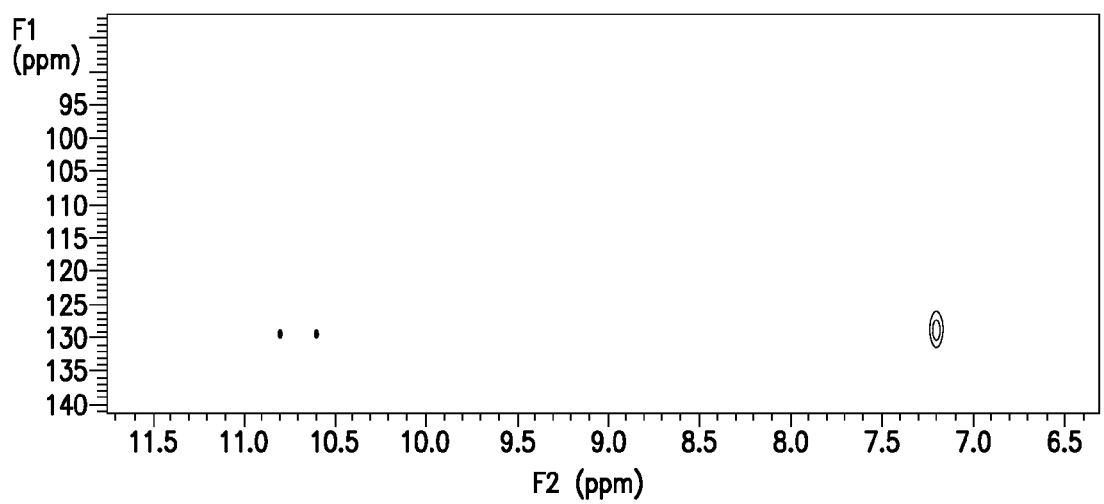
FIG. 8 is a 3D N-H J-HMBC spectrum of the melatonin sample acquired by applying the pulse sequence of FIG. 6 in the same NMR experiment.

An example of implementing the process of structure elucidation through implementation of the pulse sequence 600 of FIG. 6 will now be described in the context of a single NMR experiment carried out on a sample of melatonin. FIGS. 7 and 8 illustrate examples of spectra recorded for this example. Experimental details included the following: 128 increments in F1 and 16 increments in F2, 4 scans per increment, $sw_1$ (C-13)=32 kHz, sw2 (N-15)=3.2 kHz, sw (H-1)=12.5 kHz. FIG. 7 illustrates the N-H HSQC spectra of melatonin and FIG. 8 illustrates the F1F3 projection of the 3D N-H J-HMBC spectrum of melatonin. The one-bond H-N HSQC spectra (FIG. 7) provide information about the number of protonated nitrogen atoms in the molecule. The long-range H-N correlations in the 3D N-15 J-HMBC spectra (FIG. 8) provide further information about the position and number of the nitrogen atoms in the molecule.

It therefore can be seen that an NMR experiment performed in accordance with the present disclosure is capable of recording all the necessary information simultaneously (in a single experiment) and in parallel using multiple NMR receivers. In most cases, such an experiment avoids multiple recycling delays and hence shorter recording times. Moreover, the experiment is less prone to operator errors and instrumental variations, and ensures that all spectra are recorded under identical conditions. Experiments carried out in accordance with the invention enable single "push-button" structure determination of molecules.

It will be further understood that various aspects or details of the invention may be changed without departing from the scope of the invention. Furthermore, the foregoing description is for the purpose of illustration only, and not for the purpose of limitation—the invention being defined by the claims.

What is claimed is:

1. A NMR method of accruing spectral information from molecules by determining the structure of a sample molecule, the method comprising:
   applying an NMR pulse sequence to H and X1 nuclei of the sample molecule, wherein H designates a proton and X1 designates a magnetically active heteronucleus;
   while applying the NMR pulse sequence, acquiring two-dimensional X1-X1 correlation spectra by operating a first RF receiver tuned to the X1 frequency; and
   while applying the same NMR pulse sequence, acquiring three-dimensional X1-H correlation spectra by operating a second RF receiver tuned to the H frequency, the second RF receiver being separate and operated independently from the first RF receiver,
   wherein the spectral information on the proton and the magnetically active heteronucleus is recorded simultaneously utilizing said NMR pulse sequence and said first and second independently operated RF receivers.

2. The method of claim 1, wherein the X1 nuclei are C-13 nuclei.

3. The method of claim 1, wherein acquiring two-dimensional X1-X1 correlation spectra includes applying a double-quantum X1-X1 correlation pulse sequence to the X1 nuclei.

4. The method of claim 1, further including applying a proton decoupling pulse sequence during the double-quantum X1-X1 correlation pulse sequence.

5. The method of claim 1 further including, after acquiring two-dimensional X1-X1 correlation spectra, applying a refocusing pulse to the C-13 nuclei in accordance with a constant-time evolution sequence.

6. The method of claim 1, wherein acquiring two-dimensional X1-X1 correlation spectra includes applying a double-quantum X1-X1 correlation pulse sequence to the X1 nuclei, and further including, after acquiring two-dimensional X1-X1 correlation spectra, applying a refocusing pulse to the X1 nuclei in accordance with a constant-time evolution pulse sequence.

7. The method of claim 6, further including applying a proton decoupling pulse sequence during the double-quantum X1-X1 correlation pulse sequence and the constant-time evolution pulse sequence.

8. The method of claim 7, further including terminating the H decoupling pulse sequence after which X1-H couplings evolve for a period of time, then transferring X1 magnetization to H spins in preparation for acquiring three-dimensional X1-H correlation spectra.

9. The method of claim 8 further including, after transferring X1 magnetization to H spins, applying a refocusing pulse to the H spins and to the X1 spins, followed by acquiring three-dimensional X1-H correlation spectra.

10. The method of claim 1 further including, after acquiring two-dimensional X1-X1 correlation spectra, allowing X1-H couplings to evolve for a period of time, then transferring X1 magnetization to H spins in preparation for acquiring three-dimensional X1-H correlation spectra.

11. The method of claim 1, wherein acquiring three-dimensional X1-H correlation spectra includes acquiring X1-H single-quantum correlation and multiple-bond correlation spectra.

12. The method of claim 1, wherein acquiring three-dimensional X1-H correlation spectra includes acquiring two-dimensional X1-H correlation sub-spectra.

13. The method of claim 1, wherein acquiring two-dimensional X1-H correlation sub-spectra includes applying an X1 decoupling pulse sequence for a desired number of time increments during which X1-H couplings evolve.

14. The method of claim 1, wherein the NMR pulse sequence is applied to X2 nuclei of the sample molecule in addition to H nuclei and X1 nuclei, and X2 designates a magnetically active heteronucleus of a type other than the X1 nucleus, and further including, during the same NMR pulse sequence utilized to acquire X1-X1 correlation spectra and X1-H correlation spectra, acquiring X2 spectra.

15. The method of claim 14, wherein the X1 nuclei are C-13 nuclei.

16. The method of claim 14, wherein the X2 nuclei are N-15 nuclei.

17. The method of claim 14, wherein acquiring X2 spectra includes acquiring X2 spectra based on direct observation of X2 transverse magnetization by operating a third RF receiver tuned to the X2 frequency, the third RF receiver being separate and operated independently from the first RF receiver and the second RF receiver.

18. The method of claim 14, wherein acquiring X2 spectra includes acquiring X2-H correlation spectra by operating the second RF receiver.

19. The method of claim 18, further including allowing X1-H couplings to evolve for a first period of time, then transferring X1 magnetization to H spins in preparation for acquiring three-dimensional X1-H correlation spectra while allowing X2-H couplings to evolve for a second period of time, and then transferring X2 magnetization to H spins in preparation for acquiring X2-H correlation spectra.

20. The method of claim 14, wherein acquiring X2 spectra includes acquiring X2 spectra based on direct observation of X2 transverse magnetization by operating a third RF receiver tuned to the X2 frequency, the third RF receiver being separate and operated independently from the first RF receiver and the second RF receiver, and acquiring X2-H correlation spectra by operating the second RF receiver.

* * * * *